US012121039B2

(12) United States Patent
Grimaldi et al.

(10) Patent No.: US 12,121,039 B2
(45) Date of Patent: Oct. 22, 2024

(54) STRUCTURED VEGETABLE FAT COMPOSITIONS, A PROCESS FOR OBTAINING SAME AND USE THEREOF

(71) Applicants: CARGILL, INCORPORATED, Wayzata, MN (US); UNIVERSIDADE ESTADUAL DE CAMPINAS—UNICAMP, Campinas (BR)

(72) Inventors: Renato Grimaldi, Campinas (BR); Lireny Aparecida Guaraldo Gonçalves, Campinas (BR); Isabel Paes Manso, São Paulo (BR)

(73) Assignee: Cargill, Incorporated, Wayzata, MN (US)

( * ) Notice: Subject to any disclaimer, the term of this patent is extended or adjusted under 35 U.S.C. 154(b) by 830 days.

(21) Appl. No.: 15/314,753

(22) PCT Filed: May 29, 2015

(86) PCT No.: PCT/BR2015/050064
§ 371 (c)(1),
(2) Date: Nov. 29, 2016

(87) PCT Pub. No.: WO2015/179941
PCT Pub. Date: Dec. 3, 2015

(65) Prior Publication Data
US 2017/0112159 A1    Apr. 27, 2017

(30) Foreign Application Priority Data

May 29, 2014  (BR) .......................... 102014012953-7

(51) Int. Cl.
*A23D 9/013* (2006.01)
*A21D 2/16* (2006.01)
(Continued)

(52) U.S. Cl.
CPC ............. *A23D 9/013* (2013.01); *A21D 2/165* (2013.01); *A23D 7/013* (2013.01); *A23G 3/346* (2013.01);
(Continued)

(58) Field of Classification Search
CPC ...... A23G 2200/08; A23G 3/346; A23G 3/40; A23G 9/327; A23G 9/52; A23L 23/10; A23L 25/10
See application file for complete search history.

(56) References Cited

U.S. PATENT DOCUMENTS 5,470,598 A * 11/1995 Scavone ................. A23D 9/00
426/601
2002/0114874 A1    8/2002 Floeter et al.
(Continued)

FOREIGN PATENT DOCUMENTS

WO      199525433 A1    9/1995
WO   WO-9525433 A1 *   9/1995   ............... A23D 9/00
(Continued)

OTHER PUBLICATIONS

Brandt., "Emulsifiers in Baked Goods". Available online at https://www.naturalproductsinsider.com/archive/emulsifiers-baked-goods (Year: 1996).*

(Continued)

*Primary Examiner* — Donald R Spamer
*Assistant Examiner* — Assaf Zilbering

(57) ABSTRACT

The present invention is inserted in the sector of edible oils and fats. Basically, it relates to a vegetable fat food composition used in making food products, such as dough, margarines, cookies, ice creams, melanges, broth in cubes, sweet creams and fillings for food products such as cakes, biscuits, bonbons, and the like. And more specifically, it relates to the production of fats with low contents of saturated fatty acids based on vegetable oils and structuring agents rich in monoacylglycerols.

9 Claims, 7 Drawing Sheets

(51) Int. Cl.

| | | |
|---|---|---|
| *A23D 7/01* | (2006.01) | |
| *A23G 3/34* | (2006.01) | |
| *A23G 3/40* | (2006.01) | |
| *A23G 9/32* | (2006.01) | |
| *A23G 9/52* | (2006.01) | |
| *A23L 23/10* | (2016.01) | |
| *A23L 25/10* | (2016.01) | |
| *A23L 33/115* | (2016.01) | |
| *A61K 8/37* | (2006.01) | |
| *A61K 8/92* | (2006.01) | |
| *A61Q 19/00* | (2006.01) | |

(52) U.S. Cl.
CPC ............ *A23G 3/40* (2013.01); *A23G 9/327* (2013.01); *A23G 9/52* (2013.01); *A23L 23/10* (2016.08); *A23L 25/10* (2016.08); *A23L 33/115* (2016.08); *A61K 8/375* (2013.01); *A61K 8/922* (2013.01); *A61Q 19/00* (2013.01); *A23G 2200/08* (2013.01); *A61K 2800/10* (2013.01)

(56) References Cited

U.S. PATENT DOCUMENTS

| | | |
|---|---|---|
| 2003/0054082 A1 | 3/2003 | Koike et al. |
| 2005/0214436 A1 | 9/2005 | Doucet |
| 2010/0026768 A1 | 2/2010 | Gold et al. |
| 2010/0267681 A1 | 10/2010 | Hosoya et al. |
| 2011/0135805 A1* | 6/2011 | Doucet .................. A23D 7/013 426/606 |
| 2014/0030411 A1 | 1/2014 | Orthoefer et al. |

FOREIGN PATENT DOCUMENTS

| | | |
|---|---|---|
| WO | 2006053097 A1 | 5/2006 |
| WO | 2011143037 A1 | 11/2011 |

OTHER PUBLICATIONS

Bot, Arjen , et al., "Non-TAG structuring of edible oils and emulsions", Food Hydrocoll, 23, Elsevier, 2009, 1184-1189.

Daniel, Edmund Co, et al., "Organogels: An Alternative Edible Oil-Structuring Method", J Am Oil Chem Soc 89, 2012, 749-780.
Pernetti, Mimma , et al., "Structuring of edible oils by alternatives to crystalline fat", Curr Opin Colloid Interface Sci 12, Elsevier, 2007, 221-231.
Acevedo Nuria C et al: "Engineering the Functionality of Blends of Fully Hydrogenated and Non-Hydrogenated Soybean Oil by Addition of Emulsifiers", Food Biophysics, Springer US, Boston, vol. 9, No. 4, May 16, 2014 (May 16, 2014), pp. 368-379, XP035377284, ISSN: 1557-1858, DOI: 10.1007/S11483-014-9340-9.
Scherz H et al: "Food Composition and Nutrition Tables; Oil Soybean", Jan. 1, 2000 (Jan. 1, 2000), Food Composition and Nutrition Tables = Die Zusammensetzung Der Lebensmittal, Nahrwert-Tabellen=La Composition Des Aliments, Tableaux Des Valeurs Nutritives, Medpharm Scientific Publishers, Stuttgart, Germany, pp. 188, XP002275371, ISBN: 978-3-88763-076-8.
W Buchheim et al: "Relation Between Microstructure, Destabilization Phenomena and Rheological Properties of Whippable Emulsions", Food Structure, vol. 4, No. 2, Sep. 1, 1985 (Sep. 1, 1985), pp. 221-232, XP055207707.
Nelson Ko Ojijo et al: "Effects of monoglyceride content, cooling rate and shear on the rheological properties of olive oil/monoglyceride gel networks", Journal of the Science of Food and Agriculture, vol. 84, No. 12, Aug. 20, 2004 (Aug. 20, 2004), pp. 1585-1593, XP055117541, ISSN: 0022-5142, DOI: 10.1002/jsfa.1831.
Rogers et al: "Novel structuring strategies for unsaturated fats-Meeting the zero-trans, zero-saturated fat challenge: A review", Food Research International, Elsevier Applied Science, Barking, GB, vol. 42, No. 7, Aug. 1, 2009 (Aug. 1, 2009), pp. 747-753, XP026131983, ISSN: 0963-9969, DOI: 10.1016/J.FOODRES.2009-02-024.
Francesca R Lupi et al: "A rheological analysis of structured water-in-olive oil emulsions", Journal of Food Engineering, Barking, Essex, GB, vol. 107, No. 3, Jul. 9, 2011 (Jul. 9, 2011), pp. 296-303, XP028274306, ISSN: 0260-8774, DOI: 10.1016/J.JFOODENG.2011.07.013.
International Search Report mailed Aug. 28, 2015 for International Application No. PCT/BR2015/050064 (5 pages).
Zero trans fats from soybean oil and fully hydrogenated soybean oil: Physico-chemical properties and food applications Ana Paula B. Ribeiro a, , Renato Grimaldi a, Luiz A. Gioielli b, Lireny A.G. Gonçalves Food Research International 42 (2009) 401-410.

* cited by examiner

STRUCTURED VEGETABLE FAT COMPOSITIONS, A PROCESS FOR OBTAINING SAME AND USE THEREOF

CROSS-REFERENCE TO RELATED APPLICATIONS

This application is a national phase application of PCT/BR2015/050064, filed May 29, 2015, which claims the benefit of Brazilian Patent Application No. BR102014012953-7, filed May 29, 2014, which applications are hereby incorporated by reference herein in their entirety.

In a comprehensive way, the present invention relates to the sector of edible oils and fats. Basically, it relates to a vegetable-fat food composition used in the manufacture of food products, such as dough, margarines, cookies, ice-creams, mélanges, cube broths, sweet creams and fillings of food products such as cakes, biscuits, bonbons, and similar products. And more specifically, it relates to the production of fats with low and/or reduced contents of saturated fatty acids based on vegetable oils and structuring agents rich in monoacylglycerols.

BACKGROUND OF THE INVENTION

The replacement of partially hydrogenated fats in food products, mainly in shortenings and confectionary products constitutes, at present, a challenge, since desired properties of crystallization and texture are difficult to achieve, mainly when there is absence of trans fatty acids (REYE-SHERNÁNDES et al, 2007). In most cases, this texture is achieved by increasing the contents of saturated fatty acids ion the products, which is a further component that is nutritionally questioned.

Although numberless studies have been developed in this area, the exploitation of new raw materials and/or combinations thereof is a preponderant factor for obtaining new fatty fractions that can be employed in the widest variety of food products, without restrictions of technological or functional nature.

The crystallization of fats is a critical factor associated to the structuring and other properties of a large part of foods. The stability of many processed products is influenced by changes in the physical state of the fats and alterations in the crystallization processes, since the events of nucleation and crystalline growth take place simultaneously at different rates, because they are affected by conditions of the process, such as degree and rates of overcooling, viscosity of the medium and stirring (TORO-VAZQUEZ et al., 2005).

The structure of many food products is based on crystalline networks of totally saturated triacylglycerol (TG), known as "hardfat". The latter contain high levels of saturated fatty acids, which are among the factors that contribute to cardiovascular diseases. So, it would be desirable to have alternative pathways to increase the crystalline structure of edible oils (METIN & HARTEL, 2005).

In spite of the good structuring capability, hardfats contain a larger number of saturated fatty acids, which are considered harmful to health, since their presence in the diet is one of the factors that contribute to cardiovascular diseases (KEYS; ANDERSON & GRANDE, 1965; MENSINK et al, 2003).

The use of emulsifiers (mono- and di-acylglycerols) as structuring agents emerges as an alternative to obtaining low-sat fats with adequate consistency by virtue of their action mode, which seems to impart to the oils induction to crystallization and formation of a crystalline network that provide them with adequate textures.

Among the structural agents that have received attention in the past few years are: mono- (MG) and diacylglycerols (DG), fatty acids, fatty alcohols, waxes, wax esters, sorbitan esters and phytosterols. One can see that the most efficient agents form a small-size structuring network, preferably with non-spherical particles. The mixture of components often provides superior structuring as compared with the use of pure components. A simple analysis of the pure components can be feasible. However, the number of options provided by the mixture requires guided selection, for which understanding the underlying mechanism is essential (METIN & HARTEL, 2005).

A deep understanding of the underlying behavior of the structuring agents in lipidic phase is necessary to find such alternatives. Additional studies aimed at understanding them are essential to enable one to plan the process. This is relevant chiefly because some of the systems that are most interesting in structuring crystalline networks are constructed by mixing components.

Ingredients with limited solubility, which precipitate during the formation of a gel are capable of providing the oils with structure. The structuring agents may be macromolecules such as polymers or proteins, compounds of low molecular weight, such as fatty acids, fatty alcohols, or TG.

The interactions between the elements may be of different nature, as for instance covalent bonds, electrostatic forces, hydrogen bridges, van der Waals' forces or steric impediments. In general, the formation of a three-dimensional network is carried out by structuring the elements, which act as building blocks. Usually only a small number of building blocks are necessary to create a network. The commonest examples of this type of structure are gels and crystallized fat. These structures are used in different applications, such as pharmaceutics and cosmetics (CARRETTI; DEI & WEISS, 2005; SINGH et al, 2004).

Document US2002/0114874, for example, relates to the use and process of producing vegetable fats (*Allanblakia* sp. and *Pentadesma* sp.) in emulsions composed by triacylglycerols, the fat phase of which is a mixture of 50-99% w/w of vegetable oils and 1-50% w/w of vegetable fats. More specifically, this document foresees the preparation of a water/oil emulsion comprising from 20 to 70% of an aqueous phase dispersed in 30-80% of an oily phase, wherein the oily phase proposed, for instance, for the formation of a margarine, is constituted by a triacylglycerol containing high contents of triacyglycerol SOS, wherein S=stearic acid and O=oleic acid. Additionally, US 2002/0114874 relates to the use of the fats obtained from these plants as hardstock fat without physical or chemical modification, as long as the minimum contents of 48% of SOS is present (ranging from 45 to 50%).

The sources of triacylglycerols embraced in the US document in question are obtained from an African plant *Allanblackia*, for instance, of the species *A. floribunda* and *A. stuhlmannii*, which may present up to 60-80% of SOS and low contents of SSS, wherein S=stearic acid. The document further foresees the possibility of using another African plant coming from *Pentadesma butyracea*, of similar triacylglycerol structure (48% of SOS). As to the emulsion, it is obtained by using a liquid oily fraction (canola oil, sunflower-seed oil, cotton oil, soybean oil, olive oil or mixture of other oils) at 70% plus 30% of hardfat, subjected to crystallization with aqueous fraction often employed for preparing margarines.

Thus, document US 2002/0114874 differs from the proposed invention chiefly in that the formulated product is a water-in-oil emulsion. Besides, the structuring described in the US document takes place by adding hardfat to the fat, that is, through the most widely used technique, and is restricted to the production of margarines. Finally, it was observed that the sources indicated in the US document, in this case, fats from *Allanblackia* or *Pentadesma*, which contains in its composition 65% and 48% of triacylglycerols of the SUS type, respectively, are of difficult commercial access, which makes the use on large scale difficult due to the little offer of a regional product.

On the other hand, document US2003/0054082 relates to food compositions with oils and fats comprising from 5 to 100% w/w of monoacylglycerols (MG) and/or di-acylglycerols (DG), exhibiting Omega-3 unsaturated fatty acids ranging from 15 to 90% w/w, with a view to reduce body fat and visceral fat in treatments of obesity. More specifically, these compositions are sued in preparing foods, pharmaceutical products and pet-food or feed, providing the consumption of large amounts of monoacylglycerols (MG) and di-acylglycerols (DG), instead of using triacylgrycerols (TG).

The proposal described in the US document recommends ranges from 40 to 100%, preferably from 80-95% in the use of two combined products (in this case, MG and DG) and indicates the need to include Omega-3 fatty acid in their structure, indicating 20 to 80%, preferably from 40 to 65%, wherein MG and DG may be used either separately or mixed with each other.

Additionally, the US document proposes various feasible glyceride mixtures, with the concern of having a stability index that preserves the quality of the product worked out. For this purpose, this document suggests addition of anti-oxidant products that demonstrated oxidative stability longer than 7 hours, according to the data of Rancimat. Studies with laboratory animals also prove the reduction of obesity, according to said document.

Unlike the proposed invention, which has the objective of structuring the lipids in order to improve the technological conditions of use (without increasing the contents of saturated fatty acids), document US2003/0054082 has the objective of producing an oil or fat containing from 5 to 100% MG and/or DG, of which the oxidative stability is of at least 7 hours at 100° C., wherein the MG and/or DG contains in its composition from 15 to 90% of polyunsaturated fatty acids of the Omega-3 series, without, however, indicating high contents of DG in the oil or proposing addition of MG in high contents. This composition, according to information of the document itself, is effective for reducing body fat and visceral fat, and in preventing and treating obesity.

Document US2010/026768, for instance, describes an oil or fat composition comprising 15% w/w or more diacylglycerols, contents of unsaturated and conjugated (CLA) fatty acids of 80% w/w or more, contents of monoacylglycerols of 5% or less, protected with alpha tocoferol, providing a fat with high contents of diacylglycerols containing conjugated fatty acids to fight obesity, with high stability, wherein the CLA include the 9,11-octadecadienoic and 10-12, octadecadienoic acids, obtained by processes of conjugation with enzymes or chemical conjugation, under alkaline conditions. Trans isomers of these fatty acids should be in the range from 0.1 to 3% under aspects of odors, physiological effects, stocking stability, appearance and industrial productivity of the oil or fat.

Unlike the proposed invention, the process described in document US2010/0267681 comprises high contents of diacylglycerols and conjugated fatty acids for obtaining the proposed fat, besides requiring chemical transformation of the oils by means of known processes or processes proposed recently in the prior art, employing metallic catalysts or enzymes, these processes being totally dispensable in the present invention.

Document WO2011/143037 relates to compositions and methods for the production of natural oils, comprising from 0 to 90% triacylglycerols, from 10 to 99% combined mono- and di-acylglycerols using from 1 to 40% structuring agent (examples given with 40% talc, as active solid for structuring lapis). More specifically, it refers to the working out of lapis with products alternative to those derived from petroleum, wherein one may use, as structuring agents in the case of petroleum, kaolin, titanium dioxide, talc, feldspar, maize starch, alumina, mica and mixtures thereof. One also proposes alternative compositions with other lipidic mixtures, for example, those containing less fatty acid ester of a polyol. The main objective of document WO2011/143037, besides use vegetable oils that are less aggressive to the environment in the formulation of lapis, was to guarantee that these compounds in the process would not undergo exudation of the oil (fat Bloom).

The MGs used in the proposal described in document WO2011/143037 were selected from Dimodan HSK from Danisco, Alphadim 90 PBK from Caravan Ingredients or mixtures thereof, in the range from 15 to 25%, associated to DG. The DGs used were selected from Trancendim 120, Trancedim 130 from Caravan Ingredients or mixtures thereof. Ion formulations containing oils like TG (40-60%), these contents always completed 100%. On average, one also used a mixture of 1 to 10% for additives for dyes, besides special components like glitter.

One demonstrated tests made on lipid base containing 45-51 of TG, 19-23% of MG and DG combined, and 28-32% of structuring agent (talc), without observing any fat Bloom. The present invention differs from document WO2011/143037 chiefly in that the latter describes the use high contents of DG and MG, wherein for the application one still has the aid of an inorganic structuring agent.

Document US2011135805-A1, for instance, describes structuring compositions comprising a fat system that includes a mixture of glycerides, the structuring composition comprising at least about 50% by weight of diacylglycerols (DG) and contents of 25% by weight of monoacylglycerols (MG), based on the total weight of glycerides of the composition; and wherein the fat system comprises at least about 30% by weight of crystals with beta prima polymorphism, based on the total weight of crystals present in the fat system. The mixture of glycerol and vegetable oil, or of glycerol and a fatty acid, wherein the vegetable oil is selected from a group consisting of totally hydrogenated soybean oil, completely hydrogenated palm oil, completely hydrogenated palm stearin, totally hydrogenated coco-nut oil or totally hydrogenated canola oil, completely hydrogenated cotton-seed oil, colza oil with high contents of completely hydrogenated erucic acid, and mixture thereof. The proposal of the US document is to use products with high level of beta prima crystals, with a value of small crystal size that can aid in structuring and aerating food products, as well as to act as a barrier agent in the shelf-life. More specifically, it proposes to work out partial glycerides from the glycerolysis reaction, with the objective of obtaining a mixture containing high contents of DG and smaller amounts of TG and MG, unlike the present invention, in which the minimum contents of MG in the structuring agent is 52%.

Grimaldi, R. and Candazini, L. F. describe, in the paper "Produção de gorduras com baixo teores de saturados através da estruturação com diacilgliceróis", of 2010 (Production of fats with low contents of saturated by structuring with diacylglicerols), an edible fat produced by means of at least one of the three oils selected from vegetable cotton oil—CO, vegetable high-oleic sunflower-seed oil=HOSO and vegetable fat based on cotton—GV, together with at least one of the three actives selected from Tracedim 110, Trancedim 130-T130, and Grinsted Mono-Di HO 52F-B— GMD, components that are already known from the prior art and some with patent application filed. More specifically, for the production of the fats obtained, one employed, as additive, DG with 90% and MG with 52% at most.

In the face of the foregoing, there is a demand for obtaining fats with as low contents of saturated fatty acids as possible, without a great reduction of the product consistency, since this reduction renders the product unfeasible in the majority of used that require consistency, as is the case of biscuits fillings.

Thus, the present invention suggests, as an alternative solution in obtaining structured fat composition chiefly by producing a structured system with high thermal resistance, which are basic desirable characteristics in most products and high crystallization velocity. Besides, the structure formed keeps the oil retained in the crystalline network, without the exudation problems usually encountered in products with high contents of saturated fatty acids.

BRIEF DESCRIPTION OF THE INVENTION

The present invention relates to a PROCESS of obtaining structured edible-fat compositions and to the structured COMPOSITIONS thus obtained, characterized by comprising: (i) 1 to 15% of emulsifier, the emulsifier being derived from totally hydrogenated vegetable oils, wherein the emulsifier comprises from 52 to 100% monoacylglycerol with respect to the emulsifier weight; and (ii) at least one refined vegetable vegetable oil, and may or may not include their derivatives thereof, including fractioned or hydrogenated products, originated from the fractioning and/or hydrogenating processes, preferably vegetable oils comprising oleic and linoleic fatty acids, wherein said structured compositions contain maximum limit of 2% of trans fatty acids and exhibit contents of saturated fatty acids lower than or equal to 39% by weight with respect to the total weight of the composition, wherein the amount of vegetable oils preferably ranges from 85 to 99% by weigh with respect to the total weight of the composition.

The present invention also relates to the USE of the structured edible-fat composition in preparing food products and food products contain such as filling for application in foods selected from cakes, bonbons, and biscuits and, additionally, in preparing a food dough for application in foods selected from cakes, cookies and panettone, as well as in preparing margarines, cube broths and sweet creams, such as hazelnut cream, chocolate-flavor cream, cracking-type cream, and peanut cream. In the cosmetics area, it can be used in preparing an intermediate product to be used as one of the ingredients of cosmetic products, especially of products in which the source of lipids should be in the pasty or even liquid form.

BRIEF DESCRIPTION OF THE FIGURES

FIG. 6(b) deals with totally hydrogenated soybean oil (hardfat) comprising 100% of triacylglycerols (HF—Soyaban); FIG. 6(c) refers to an emulsifier comprising a mixture of mono- and di-acylglycerols, wherein the portion of monoacylglycerols corresponds to 52% (MG+DG); FIG. 6(d) refers to a structured composition based on sunflower-seed oil with high oleic contents (HOSO) and 10% of emulsifier comprising a mixture of mono- and di-acylglycerols, wherein the portion of monoacylclycerols corresponds to 52% (MG+DG+HOSO); FIG. 6(e) refers to a pure compound comprising 90% of monoacylglycerols (MG); FIG. 6(f) refers to a structured composition based on sunflower-seed oil with high oleic content (HOSO) comprising 10% of a pure compound comprising 90% of monoacylglycerols (MG); FIG. 6)g) deals with a totally hydrogenated palm oil (hardfat) comprising 10% of triacylglycerols (HF Palma).

FIG. 9(*a*) refers to a comparison between the heights of the samples in millimeters. FIG. 9(*b*) refers to a comparison of the density of the samples in g/cm3. FIG. 9(*c*) relates to a comparison of the specific volumes of the samples ion cm3/g. FIG. 9(*d*) refers to a comparison of the texture of the samples in gram-force.

FIG. 10(*a*) refers to a comparison between the heights of the samples in millimeters. FIG. 10(*b*) refers to a comparison of the density of the samples in g/cm3. FIG. 10(*c*) refers to a comparison of the specific volumes of the samples in cm3/g. FIG. 10(*d*) refers to a comparison of the texture of the samples ion gram-force.

DETAILED DESCRIPTION OF THE INVENTION

Figure 1:
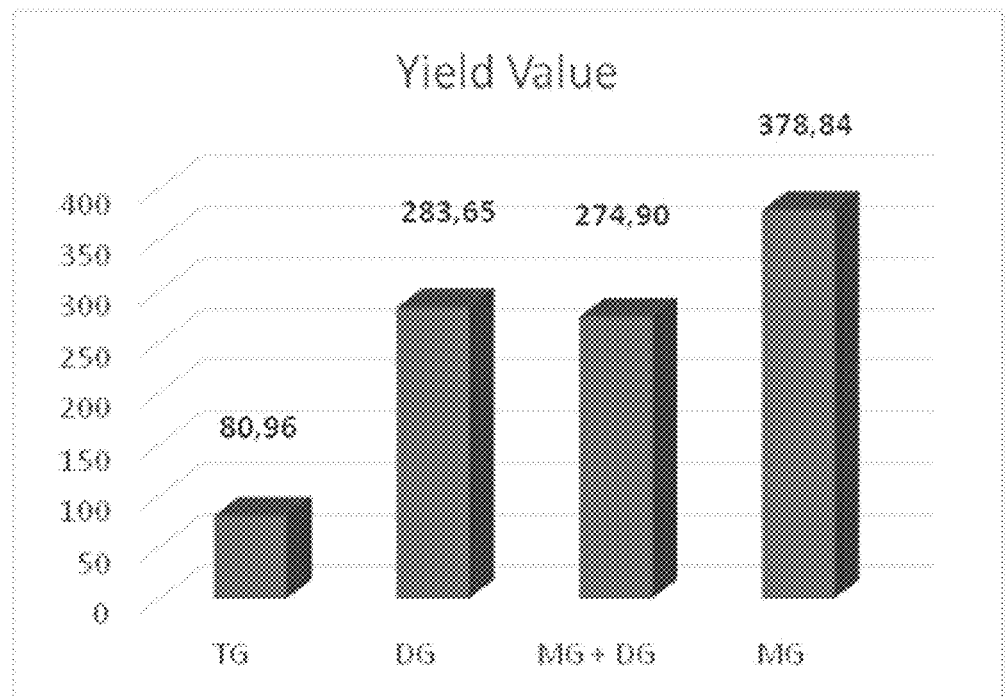
FIG. 1 indicates the results referring to texture (T=25° C.) of four (4) samples of sunflower-seed oil with high oleic content, structured with 10% of: i) a totally hydrogenated vegetable oil containing 100% of triacylglycerols (TG); ii) an emulsifier comprising 90% of diacylglycerols (DG); iii) one emulsifier comprising a mixture of monoacylglycerols and diacylglycerols (MG+DG), with 52% of monoacylglycerols; and iv) an emulsifier comprising 90% of monoacylglycerls (MG). The results prove that the capability of forming a stable crystalline network on the part of the monoacylglycerols is much superior to that of other structured compositions with triacylglycerols and diacylglycerols.

The examples given herein are intended only to exemplify one of the numberless ways to carry out the invention, but without limiting the scope thereof. In a first aspect, the present invention relates to a PROCESS for obtaining structured edible-fat compositions comprising the following main steps:

a. in a reactor provided with a sleeve, adding at least one vegetable oil selected from refined vegetable oils, their derivatives and the mixture thereof, originated from the fractioning and/or hydrogenating processes, preferably vegetable oils that are source of oleic and linoleic acids;

b. heating, under constant stirring, the vegetable oil added in step (a) at a temperature that guarantees complete melting of the emulsifier to be added in the following step, said temperature preferably ranging from 70 to 90° C., depending on the composition of fatty acids present in the emulsifier;

c. under constant stirring and heating at a temperature ranging from 70 to 90° C., adding 1 to 15% by weight, based on the total weight of the composition, of an emulsifier to the oil previously heated in step (b), said emulsifier being derived from totally hydrogenated vegetable oils and comprising a mixture of mono- and di-triacylglycerols, the portion of monoacylglycerol of the emulsifier ranging from 52 to 100% based on the emulsifier weight;

d. obtaining a structured fat composition (in its liquid phase);

e. keeping the structured composition obtained in step (d) under constant stirring and heating at a temperature ranging from 7 to 90° C., until complete dispersion of the emulsifier in the oil;

f. subjecting the structured composition in the liquid phase obtained in step (c) to a plasticizing process capable of enabling one to obtain a homogeneous structured fat composition (in its solid phase) and in its more stable crystalline phase; and obtaining a homogeneous structured fat composition comprising maximum limit of 2% of trans fatty acids and contents of saturated fatty acids lower than or equal to 39% by weight with respect to the total weight of the composition wherein, alternatively the steps (a) to (d) may be replaced by the steps of:

(i) previously adding the emulsifier to a portion of the vegetable oil, for instance, at a massic emulsifier/vegetable oil ratio of 1:1, in a reactor provided with a sleeve, kept at a temperature ranging from 70 to 90° C., for obtaining a slurry of the composition to aid in dispersing the emulsifier ion the total volume of oil used in said composition, wherein, for this previous addition of the emulsifier to the oil, one may use smaller-size reactors; and (ii) obtaining a structured fat composition in slurry form.

The product obtained in step (e) may be transported and marketed in its liquid form, and should be plasticized and/or crystallize din at its final destination, for instance, the user company, in a later step, always keeping a temperature that guarantees its liquid form to prevent re-crystallization of the emulsifier. However, due to the low contents of saturated fatty acids in the product, the user company should not stock this product in its liquid form too long, since this may cause oxidation of the structured composition. Even after transportation for stocking the product, it should be at a temperature that guarantees its maintenance in liquid form, but at the same time stocking it for a long time may cause accelerated oxidation.

In a preferred embodiment of the present invention, the reactor provided with a sleeve described in step (i) above is a reactor with scale smaller than the reactor of step (a), and the structured fat composition obtained in step (ii) should be transferred to a reactor of a scale similar to that of step (a) after step (e).

In terms of process, the invention described herein represents an advance in the prior art, chiefly because there is no need for interesterification reaction, since one uses liquid oils, which eliminates steps within the process. Additionally, after the plasticizing step, said process enables one to obtain structured fat compositions with a stable crystalline network, which enables the product to remain with the same structure, even with variations in room temperature (T=25° C.). This characteristic is important to prevent exudation (migration) of liquid oil. Thus, one understands by "stable crystalline network" that network that can be kept for a long time without exudation. Another important point is that the plasticized (crystallized) product exhibit a performance with high plasticity, which guarantees the handling thereof even with variations in temperature.

Consequently, in a second aspect, the present invention relates to a structured composition comprising:
(I) 1 to 15% by weight of an emulsifier with respect to the total weight of the composition, the emulsifier being derived from totally hydrogenated vegetable oils, the emulsifier ranging from 52 to 100% monoacylglycerol with respect to the emulsifier; and
(II) at least one refined vegetable oil, originated from the fractioning and/or hydrogenating processes, preferably vegetable oils comprising oleic and linoleic fatty acids, with respect to the total weight of the composition, wherein:
the amount of vegetable oils is preferably from 85 to 99% by weight with respect to the total weight of the composition; wherein said structured compositions contain maximum limit of 2% trans fatty acids and exhibit contents of saturated fatty acids lower than or equal to 39% by weight, based on the total weight of the composition; wherein the useful vegetable oils of the present invention are any oils selected from refined vegetable oils, their derivatives and mixture thereof, originated from the fractioning and/or hydrogenating processes.
the structured fat composition provided by the present invention exhibits maximum contents of 39% saturated fatty acids from vegetable oils and with fat characteristics, it being understood that results with contents lower than 25% already exist; and considering that the contents of saturated fatty acids of the proposed structured compositions vary according to the vegetable oil employed, with the oil having high oleic contents (HOSO), for instance, it was possible to obtain structured compositions with 16% of saturated fatty acids;
the emulsifiers employed should be derived from totally hydrogenated vegetable oils; the index of iodine around 2, for example, is an indication of the degree of saturation of the emulsifiers.

The composition may further comprise a mixture of fatty acid mono- and di-glycerides emulsifier and propylene glycol ester.

In terms of product, the invention described herein represents an advance in the prior art, since it uses bases of vegetable oils with reduced contents of saturated fatty acids and uses emulsifiers rich in monoacylglycerols, which act as structuring agents of the vegetable oils.

Additionally, the structured fat compositions provided by the present invention proved to be an alternative in situations in which the vegetable oils in their natural (liquid) form cannot be used in preparing products where a sufficient consistency is necessary for maintaining the lipidic phase, which may be mixed with sugar, in the case of fillings, or even emulsions, as is the case of margarines.

In a third aspect, the present invention further relates to the use of the structured fat composition in the food area, more specifically in preparing food products in which said fat should have a behavior of high plasticity and rapid crystallization, as are the cases of filler of biscuits, bonbons, among others, margarines, mélanges, and ice creams.

In a fourth aspect, the present invention further relates to the use of the structured fat composition in the food area, more specifically in preparing food products in which said fat should have a behavior of rapid crystallization, as is the case of broth cubes.

In a fifth aspect, the present invention further relates to the use of the structured fat composition in the food area, more specifically in preparing food products such as sweet creams such hazelnut cream, chocolate cream, cracking cream and peanut cream, these creams exhibiting plasticity/spreadability, homogenous mouthfeel, and thermal stability of the product, preventing the separation of oil from the sweet cream along the shelf-life thereof.

Other uses may also comprise the preparation of dough, preferably foods selected from cakes, panettone, cookies and any other food whose fat portion has a behavior that provides better incorporation of ingredient and air ion the dough during the beating process.

The present invention further relates to food products comprising a structured fat composition.

Such products may exhibit one or more of the behaviors of:
a. keeping the texture at a temperature range from 20 to 30° C.;
b. crystalizing in approximately 5 minutes at a temperature of 25° C., achieving crystallization of the maximum solid contents in up to 30 minutes; and/or
c. exhibiting greater resistance and being capable of remaining solid even at the body temperature; and/or
d. providing better incorporation of ingredients and air into the dough during the beating process; and/or
e. imparting thermal stability to the product, without occurrence of separation of oil throughout the shelf life.

The food product may further be grouped by a behavior as follow:
i) when the food product exhibits the behavior (a) and (b), it is selected from margarines, mélanges, ice-creams, and fillers (of biscuits, bonbons, among others);
ii) when the food product exhibits the behavior (b), it is cub broths;
iii) when the food product exhibits the behavior (c), it is selected from cakes, bonbons, and biscuits;
iv) when the food product exhibits the behavior (d), it is selected from cake dough, panettone dough, and cookie and biscuit dough;
v) when the food product exhibits the behavior (e), it is selected from sweet creams, including hazelnut cream, chocolate-flavor cream, cracking-type cream, peanut cream.

For the purpose of the present invention, one understands by "high plasticity" the maintenance of texture chiefly in a temperature ranging from 20 to 30° C. Products with low plasticity have a marked drop in texture at this temperature. Fats with plastic characteristics are widely desired in most products, especially margarines and fillings.

For the purpose of the present invention, one understands by "rapid crystallization" a characteristic that can be viewed in the crystallization isotherms, wherein it is possible to verify the increase in the contents of solids as a function of the time. Thus, the products that exhibit this characteristic are called products of rapid crystallization. As an example, we can cite as a rapid-crystallization product that one that, at a temperature of 25° C., is crystallized in about 5 minutes and manages the stabilization of the maximum contents of solids (that is, its crystals are stabilized) in up to 30 minutes, which guarantees a more stable product.

For the purpose of the present invention, one understands by "behavior that provides better incorporation of ingredients" the behavior that helps in preparing the product, facilitating the incorporation of its ingredients.

For the purpose of the present invention, one understands by "behavior that provides better incorporation of air" the behavior that enables retention of air incorporated/formed during the preparation of the product, to be viewed by the volume of cakes and overrun in ice-creams, for example.

For the purpose of the present invention, one understands by "thermal stability" the capability of keeping its main characteristics of homogeneity/structure along the time, with thermal variations to which the product may be subjected.

For the purpose of the present invention, one understands by "mélanges" a mixture between margarine and butter.

For the purpose of the present invention, one understands by "cracking-type cream" any sweet cream that comprises cracking particles in its composition.

Consequently, the present invention relates to structured fat compositions for specific applications. It further relates to products containing such a composition.

For the Preparation of Fillings for Application in Foods Selected from Cakes, Bonbons, and Biscuits:

A structured composition for application in preparing a filling, a product that requires "more structure", that is, requires more consistency and is capable of remaining solid even at body temperature (~37° C., said composition comprising: (i) from 1 to 15% by weight of an emulsifier, preferably from 3 to 10% with respect to the total weight of the composition, wherein the emulsifier should be derived from totally hydrogenated vegetable oils, the monoacylglycerol portion of the emulsifier ranging from 52 to 100% by weight of monoacylglycerol with respect to the emulsifier weight; and (ii) at least one refined vegetable oil, originated from fractioning and/or hydrogenating processes, wherein said structured compositions contain maximum limit of 2% of trans fatty acids and exhibiting contents of saturated fatty acids lower than or equal to 39% by weight with respect to the total weight of the composition. Preferably, the vegetable oils that are sources of oleic and linoleic fatty acids are used in the amount of 85 to 99% by weight, preferably from 90 to 98% by weight, based on the total weight of the composition.

Considering that the base of the fillings comprise chiefly a mixture between fat and sugar, the structured fat composition provided by the present invention ends up being responsible for maintaining the solid structure of the filling. If for the preparation of the filling one used a liquid oil, for instance, the filling would be liquid.

For the Preparation of Food Dough for Application in Foods Selected from Cakes, Cookies and Panettone:

A structured composition for application in preparing food dough for application in foods selected from cakes, cookies, panettone, and any other food whose fat portion constituting it has a behavior that provides better incorporation of ingredient and air into the dough during the beating process, wherein these foods require less consistency and maintenance of the solid structure is not so important, said composition comprising: (i) from 1 to 15% by weight of an emulsifier, preferably from 2 to 10% with respect to the total weight of the composition, wherein the emulsifier should be derived from totally hydrogenated vegetable oils, the emulsifier ranges from 52 to 100% by weight of monoacylglycerol with respect to the weight of the emulsifier; and (ii) at least one refined vegetable oil, originated from the fractioning and/or hydrogenating, wherein said structured compositions contain maximum limit of 2% of trans fatty acids and exhibit contents of saturated fatty acids lower than or equal to 39% by weight with respect to the total weight of the composition. Preferably, the vegetable oils that are sources of oleic and linoleic fatty acids are used in the amount ranging from 85 to 99% by weight, preferably from 90 to 98% by weight, based on the total weight of the composition.

Specifically in this type of application, in which less consistency is required and, on the other hand, the use of liquid oils is not very feasible, because the oxidation problems would be quite serious, the employ of the structured fat composition provided by the present invention would be useful, since the emulsifier of said composition ends up acting on the better dispersion of the components of the dough.

For the Preparation of Margarines:

A structured composition for application in preparing margarine, comprising, for example: (i) from 1 to 15% by weight of an emulsifier, preferably from 3 to 10%, with respect to the total weight of the composition, wherein the emulsifier should be derived from totally hydrogenated vegetable oils, the emulsifier ranges from 52 to 100% of monoacylglycerol with respect to the weight of the emulsifier; and (ii) at least one refined vegetable oil, originated from the fractioning and/or hydrogenating processes, wherein said structured compositions contain maximum limit of 2% of trans fatty acids and exhibiting contents of saturated fatty acids lower than or equal to 39% by weigh with respect to the total weight of the composition. Preferably, the vegetable oils that are sources of oleic and linoleic fatty acids are used in the amount ranging from 85 to 99% by weight, preferably from 90 to 98% with respect to the total weight of the composition.

For the Preparation of Broth in Cubes:

A structured composition for application in preparing broth in cubes, comprising, for example: (i) from 1 to 15% by weight of an emulsifier, preferably from 3 to 10%, with respect to the total weight of the composition, wherein the emulsifier should be derived from totally hydrogenated vegetable oils, the emulsifier ranges from 52 to 100% by weight of monoacylglycerol with respect to the weight of the emulsifier; and (ii) at least one refined vegetable oil, originated from the fractioning and/or hydrogenating processes, wherein said structured compositions having maximum limit of 2% of trans fatty acids and exhibiting contents of saturated fatty acids lower than or equal to 39% by weigh with respect to the total weight of the composition, Preferably the vegetable oils that are sources of fatty oleic and linoleic acids, in the amount ranging from 85 to 99% by weigh, preferably from 90 to 98% by weigh, based on the total weight of the composition.

Specifically in this type of application, the cube broth prepared with the structured composition provided by the present invention brings about ease in melting, chiefly in preparing soups, does not cause waxiness when applied, chiefly in soups, besides exhibiting thermal stability, preventing the separation of the oil from the product during its shelf-life.

For the Preparation of Ice Creams:

A structured composition for application in preparing a an ice cream, comprising, for example: (i) from 1 to 15% by weight of an emulsifier, preferably from 3 to 10%, with respect to the total weight of the composition, wherein the emulsifier should be derived from totally hydrogenated vegetable oils, the emulsifier ranges from 52 to 100% by weight of monoacylglycerol based on the weight of the emulsifier; and (ii) at least one refined vegetable oil, originated from the fractioning and/or hydrogenating processes, wherein said structured compositions contain maximum limit of 2% of trans fatty acids and exhibiting contents of saturated fatty acids lower than or equal to 45% by weigh with respect to the total weight of the composition; preferably, the vegetable oils that are sources of oleic and linoleic fatty acids are used, in the amount ranging from 85 to 99% by weight, preferably from 90 to 98% by weight based on the total weight of the composition.

For the Preparation of Sweet Creams:

A structured composition for application in preparing sweet creams, such as hazelnut cream, chocolate cream, cracking-type cream and peanut cream, which require plasticity/spreadability and thermal stability of the product, said composition comprising: (i) from 1 to 15% by weight of an emulsifier, preferably from 3 to 10%, with respect to the total weight of the composition, wherein the emulsifier should be derived from totally hydrogenated vegetable oils, the emulsifier ranging from 52 to 100% by weigh of monoacylglycerol based on the weight of the emulsifier; and (ii) at least one refined vegetable oil, originated from the fractioning and/or hydrogenating processes, wherein said structured compositions contain maximum limit of 2% of trans fatty acids and exhibiting contents of saturated fatty acids lower than or equal to 35% by weigh with respect to the total weight of the composition; preferably, the vegetable oils that are sources of oleic and linoleic fatty acids are used, in the amount ranging from 85 to 99% by weight, preferably from 90 to 98% by weight based on the total weight of the composition.

For the Preparation of Intermediate Products for Application in the Cosmetics Area:

Additionally, the invention relates to the use of the structured fat composition in the cosmetics area, more specifically in preparing cosmetic products with "pasty or creamy consistency". At present, there is a demand for the use of other fats, and even wax, in conjunction with vegetable oils, so that the lipidic composition can reach a fat consistency, that is, so that it can be solid at room temperature, since for the area of "Oils and Fats" one understands by "oils" products that are liquid at room temperature; one understands by "fats" products that are solid at room temperature, and one understands by "pasty (creamy)" products with a pasty characteristic similar to a milk cream. Thus, the structured fat composition provided by the present invention represents an alternative to meet this demand, and it may be, for example, an intermediate product in the cases in which it is necessary to have a base from the liquid oils, but it is not possible due to the nature itself of these oils and, in these conditions, it is necessary to use an ingredient or product capable of structuring them, or emulsions in general, especially where it is necessary to use liquid vegetable oils that do not impart structure to the products formed.

Especially in the use in the cosmetic branch, the present invention enables the utilization of various oleaginous sources in products in which the lipid source should be in the pasty or even liquid form.

For the purpose of the present invention, one understands by "pasty or creamy consistency" the one similar to a milk cream, in which the texture values (Yield value) are lower than 50 g/cm2.

Consequently, the present invention elates to a structured composition for application in the formulation of cosmetic products comprising: (i) from 1 to 15% by weight with respect to the total weight of the composition, wherein the emulsifier should be derived from totally hydrogenated vegetable oils, the emulsifier ranging from 52 to 100% by weight of monoacylglycerol based on the weight of the emulsifier; and (ii) at least one refined vegetable oil, originated from the fractioning and/or hydrogenating processes; preferably, the vegetable oils that are sources of oleic and linoleic fatty acids are used, in the amount ranging from 85 to 99% by weight, preferably from 90 to 97% by weight based on the total weight of the composition.

Besides the aspect of enabling the use of higher contents of liquid oils, the presence of the emulsifiers enables one to increase the consistency of these oils and to enhance the stability of the crystalline network of the cosmetic products, for instance, even with variation in temperature. Various cosmetic products are carried, especially by women, in bags, where the temperature varies much and may cause destabilization of the product, with appearance of the free oil. In this case, the emulsifier can act in a parallel manner and assume two functions: that of a structuring agent and hat of an emulsifier, with greater dispersion of the ingredient of the cosmetic product.

Results and Examples of Embodiment

Results Referring to the Texture of the Samples:

The analysis of the texture reports the resistance to cone penetration under specific conditions of the analysis and its final value is differently related to the crystalline network formed. The more stable networks produce products with greater resistance to cone penetration. The samples of the compositions underwent a controlled-temperature process where one intended to achieve stabilization of the polymorphic forms at the reading temperature. The values shown in FIG. 1 indicate that the structured composition rich in monoacylglycerols reached the highest texture value at 25° C., which proves its greater capability of structuration and formation of a more stable crystalline network. The samples evaluated and presented in FIG. 1 were structured with sunflower-seed oil with high oleic content—HOSO (TG), emulsifiers with 90% diacylglycerols (DG), mixture of monoacylglycerols and diacylglycerols, with 52% of monoacylglycerols (MG+DG) and emulsifier with 90% of monoacylglycerols (MG), all of them with 10% of said emulsifier. The capability of forming a stable crystalline network is observed in the composition rich in monoacylglycerols, demonstrating to be significantly superior to that of other structured compositions with triacylglycerols and diacylglycerols.

Figure 2:
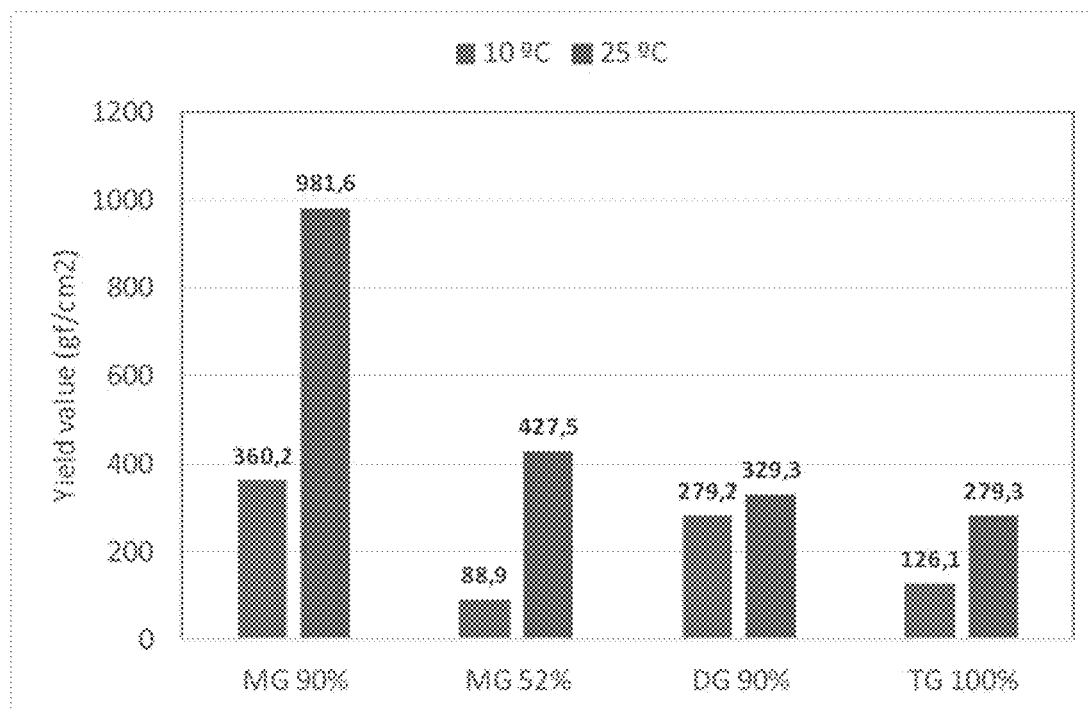
FIG. 2 indicates the results referring to the texture of four (4) samples of soybean oil structured with 10% of: an emulsifier containing 90% of monoacylglycerols (MG 90%); ii) an emulsifier containing 52% of monoacylglycerols (MG 52%); iii) an emulsifier containing 90% of diacylglycerols (DG 90%); and iv) an emulsifier containing 100% of triacylglycerols (TG 100%), at temperatures ranging from 10 to 25° C.

On the other hand, the texture values (Yield values) shown in FIG. 2 referring to the samples of soybean oil structured with 10% of: i) and emulsifier containing 90% of monoacylglycerols (MG 90%); ii) an emulsifier containing 52% of monoacylglycerols (MG 52%); iii) an emulsifier containing 90% diacylglycerols (DG 90%); and iv) an emulsifier containing 100% of triacylglycerols (TG 100%), at a temperature ranging from 10 to 25° C., demonstrate that at 10° C. the soybean-oil sample structured with 10% of the emulsifier containing DG 90% exhibits greater texture than the oil structured with the emulsifier containing MG 52%. However, at 25° C., the texture values (yield values) decrease much, keeping the tendency of the oil structured with emulsifier containing MG 90%, MG 52%, DG 90% and TG 10%.

FIG. 2 further shows that, even starting from a compound with a higher melting point, in this case, oils structured with emulsifier containing 100% triacylglycerols (TG 100%), these are not capable of providing a structure that behaves as a fat suitable for the preparation of food products.

For the purpose of the present know-how, one understands by "structured product" those products with solid visual aspect. The measurements of texture help ion quantifying the degree of this structuring and of the crystalline network formed.

Results Referring to the Crystallization Isotherms (T=25° C.):

The crystallization velocity is an important parameter in the production of food products, since in various processes the residence time of the fat or of the product inside the crystallizer or plasticizer is too short. The crystallization reaction is an exothermic process, and the time necessary to achieve stabilization of the polymorphic form is fundamental to guarantee stability of the product formulated. The crystallization isotherm, carried out through the Nuclear Magnetic Resonance (NMR) evaluates the crystallization performance of the products at a determined temperature, with evaluation of parameters such as Induction time (It/Ti), where the crystallization and the maximum contents of solids (%), where the product has reached stabilization at the reading temperature.

TABLE 1

Crystallization parameters (25° C.) in samples of structured compositions

|  | DG | MG | MG + DG | TG |
|---|---|---|---|---|
| Induction time (min) | 5 | 3 | 3 | 10 |
| Maximum contents of solids (%) | 6.6 | 10.8 | 7.7 | 8.5 |

Figure 3:
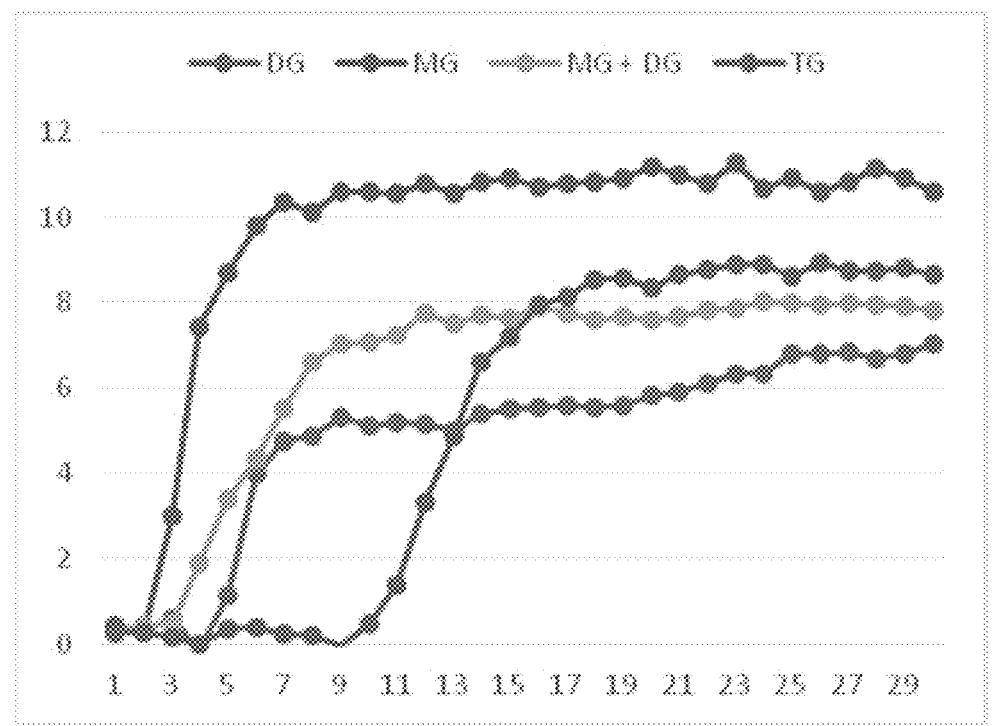
FIG. 3 indicates the results referring to isotherms of crystallization (T=25° C.) of four (4) structured compositions based on refined soybean oil comprising 10% of: i) an emulsifier comprising 90% of diacylglycerols (DG); ii) an emulsifier comprising 90% of monoacylglycerols (MG); iii) an emulsifier comprising a mixture of monoacylglycerols and diacylglicerols (MG+DG), with 52% of monoacylglycerols; and iv) a totally hydrogenated vegetable oil containing 100% of triacylglycerols (TG).

FIG. 3 shows that the compositions structured with (MG) and (MG+DG) were the ones that exhibited shorter induction times, whereas the composition structured with MG exhibited the highest contents of solids, which characterizes a more consistent product, with more cohesive and homogeneous crystalline network.

Figure 4:
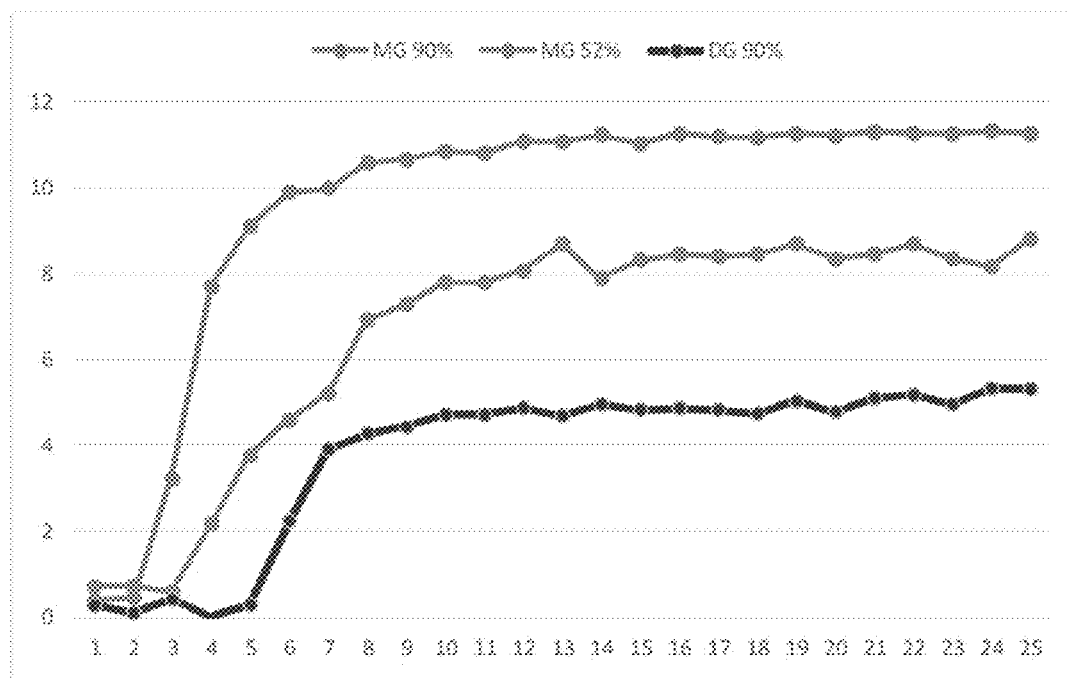
FIG. 4 indicates the results referring to the crystallization isotherm (T=25° C.) in structured composition based on refined soybean oil comprising 10% of emulsifiers containing 90% of monoacylglycerols (MG 90%); 52% monoacylglycerols (MG 52%); and 90% diacylglycerols (DG 90%).

With a view to demonstrate that the behavior of the structured fat compositions provided by the present technology remains the same, regardless of different sources of vegetable oils used, FIG. 4 presents the results of the crystallization isotherms (T=25° C.) for structuring the refined soybean oil as a source of vegetable oil, using 10% of emulsifier selected from MG 90%, MG 52%, DG 90%. The results further show that the compositions structured with emulsifiers rich in monoaclyglycerols exhibit higher contents of solids, that is greater capability of structuring, whereas the compositions rich in diacyglycerols (in this case, with DG 90%) exhibit lower contents of solids and, as a result, smaller structuring capability.

Figure 5:
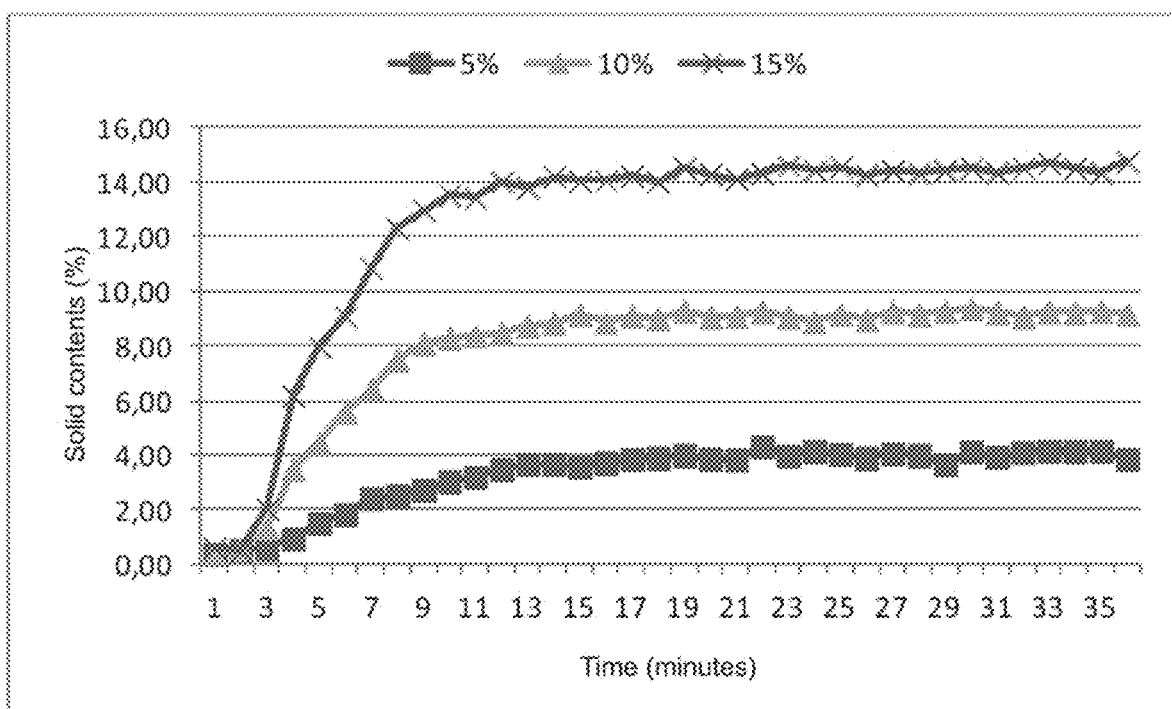
FIG. 5, for instance, presents the results of the crystallization isotherms (T=25° C.) in structured compositions based on sunflower-seed oil with high oleic contents comprising 5, 10 and 15% of an emulsifier containing 52% of monoacylglycerols (MG52%).

An additional objective is to show that the structured fat composition provided by the present technology enhances its structuring capability as the contents of solids increase. FIG. 5, for instance, presents the results of the crystallization isotherms (T=25° C.) for structuring sunflower-weed oil as source of vegetable oil using 5, 10 and 15% of an emulsifier containing 52% of monoacylglycerols (MG 52").

Figure 6:
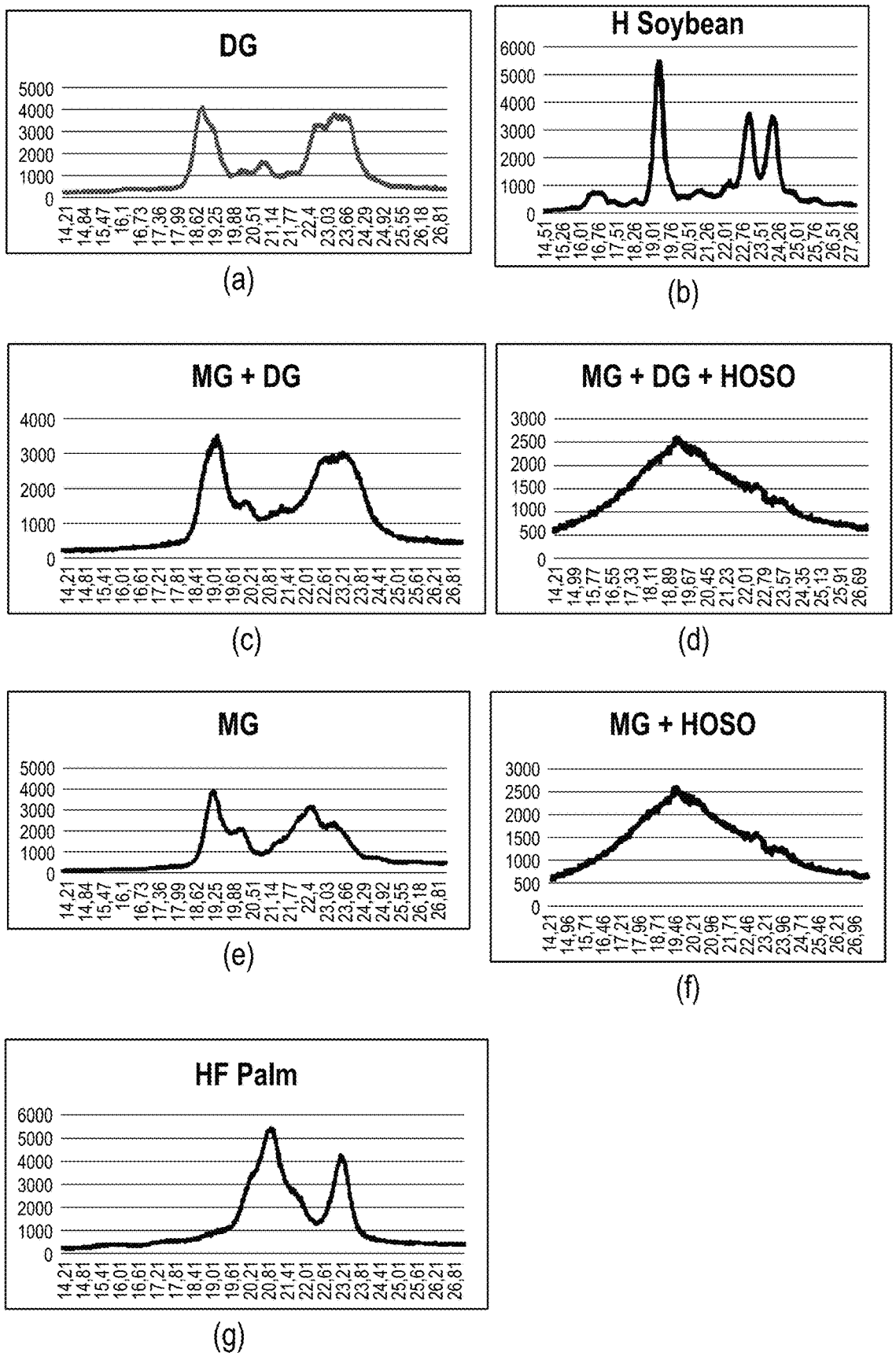
FIG. 6 indicates the results referring to the X-Ray diffractograms at 25° C. of six (6) samples. They are: FIG. (6)a) refers to a pure compound comprising 90% of diacylglycerols (DG)

Results Referring to X-Ray Diffragrams:

The X-ray diffraction is a technique that enables one to identify the predominant crystalline form in the structured product. Polymorphism is a characteristic of the fats and a fundamental aspect ion plasticizing products such as margarines and biscuits fillings, since in this step it was possible to achieve the polymorphic form of greater stability or else the desired polymorphic form for the product to be formulated. As can be observed in FIG. 6, sources of totally hydrogenated soybean oils have the tendency of crystallization in the beta (P) form, whereas the source of palm has the tendency to crystallization in the beta prima (R') form. The structured composition, due to the great amount of vegetable oils, ends up exhibiting an amorphous behavior at 25° C., since the oil is liquid, in spite of the solid appearance. Although these are behaviors different from those exhibited by triacylglycerol molecules, the emulsifiers containing monocylglycerols and diacylglycerols exhibit polymorphism with tendency of beta (13) form, characteristic of products with greater thermal stability.

Comparative Example for Biscuit Filling

For comparative purposes, one prepared samples of biscuit filling by using samples of the present invention in comparison with the biscuit filling using a prior-art reference fat.

The base formulations for the biscuit filling with base flavor, the following proportions shown in the table below were followed:

| Ingredient | Percentage |
|---|---|
| Sugar | 61.8 |
| Reference/test sample | 34.0 |
| Cocoa powder | 4.0 |
| Soybean lecithin | 0.2 |
| TOTAL | 100.00 |

In the reference formulation one used interesterified fat, base cotton and palm, with 50% of saturated fats and 2% of trans fats based on the weight of the interesterified fat.

As tests samples one used two different formulations of structured fat compositions, as described in the present invention, namely: #35 and #36.

The #35 comprises a structured fat composition, base soybean and palm, with 25% of saturated fats, 2% of trans fats and 7% of emulsifier (52% by weight of monoacylglycerol based on the weight of the emulsifier) by weight based on the weight of the structured fat composition.

The #36 comprises a structured fat composition, base soybean and palm, with 28% of saturated fats, 2% of trans fats and 2% of emulsifiers (52% by weight of monoacylglycerol based on the weight of emulsifier) by weight based on the weight of the structured fat composition.

The preparation of the formulations was carried out as described hereinafter.

Initially the reference fat or the test sample was mixed to soybean lecithin under constant beating for 1 minute for homogenization, then one added sugar, aroma and cocoa under constant beating for 1 minute and 30 seconds for homogenization. The biscuits were filled in the proportion of 28% of filling and 72% of crust.

The samples were tested for the texture of its fillings.

Figure 7:
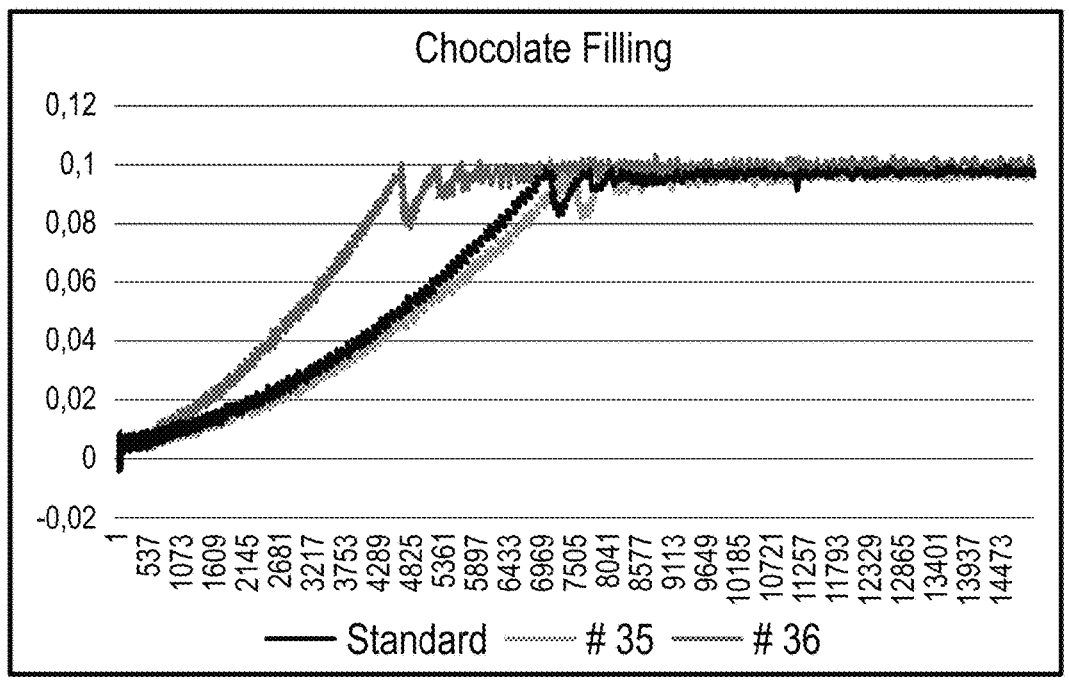
FIG. 7 is a comparative graph, Kilogram force per time in seconds, texture of biscuit filling between standard sample using a reference fat based on cotton and palm, with 50% of saturated fat and test samples using the samples #35 and #36, comprising a structured fat composition, based on soybean and palm, with 25% and 28% of saturated fats, respectively, and 2% of trans fats and 7% of emulsifier (52% of monoacyglycerol).

The performance of the textures of the test samples (#35 and #36), containing 25 and 28% of saturated, respectively, was similar to that of the reference sample containing 50% of saturated, with maximum force, which measures the resistance to penetration, at the value of 100 g, as can be seen in the graph of FIG. 7.

A third test sample was produced, which comprised a structured fat composition, base soybean and palm, with 34% of saturated fats, 2% of trans fats and 2% of emulsifier (52% by weight of monoacylglycerol) by weight based on the weight of the structured fat composition, and compared with the reference sample as defined above in a shelf-life and sensorial study.

The shelf-life and sensorial study was carried out by 4 to 6 expert evaluators with samples stored during the 8-week period at 38° C. and 80% of UR.

The filled biscuits were evaluated, and the reference was quantified as being mark 3. The scale used varies from 0 to 5 points. Marks lower than 3 represent performance superior to the standard, whereas marks lower marks refer to inferior performance. The attributes evaluated were as follows:
a. crust adhesiveness;
b. oil escape
c. waxiness in the mouth
d. global acceptance.

Figure 8:
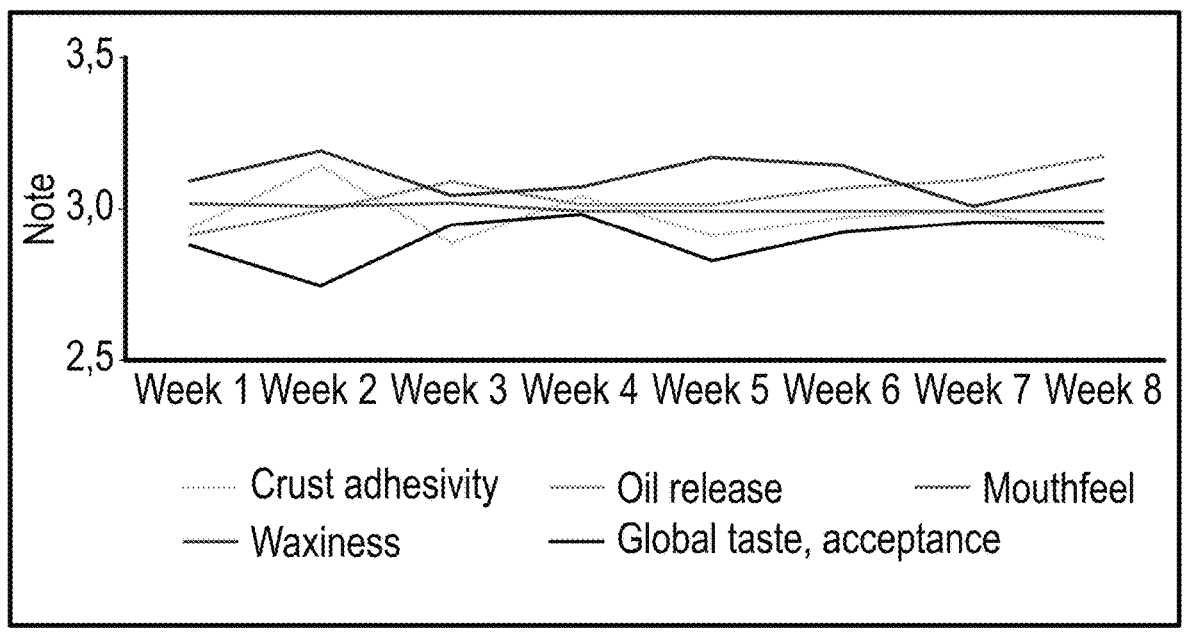
FIG. 8 is a graph of sensorial analysis of biscuit filling, wherein the standard sample was given mark three, wherein marks higher than three indicate marks higher than standard and lower than three marks indicate marks lower than standard. The standard sample uses a reference fat based on cotton and palm, containing 50% of saturated fats and a test sample, called sample 1, comprises a structured fat composition, based on soybean and palm, with 34% saturated fats, 2% trans fats an 2% emulsifiers (52% of monoacylglycerol).
Figure 9:
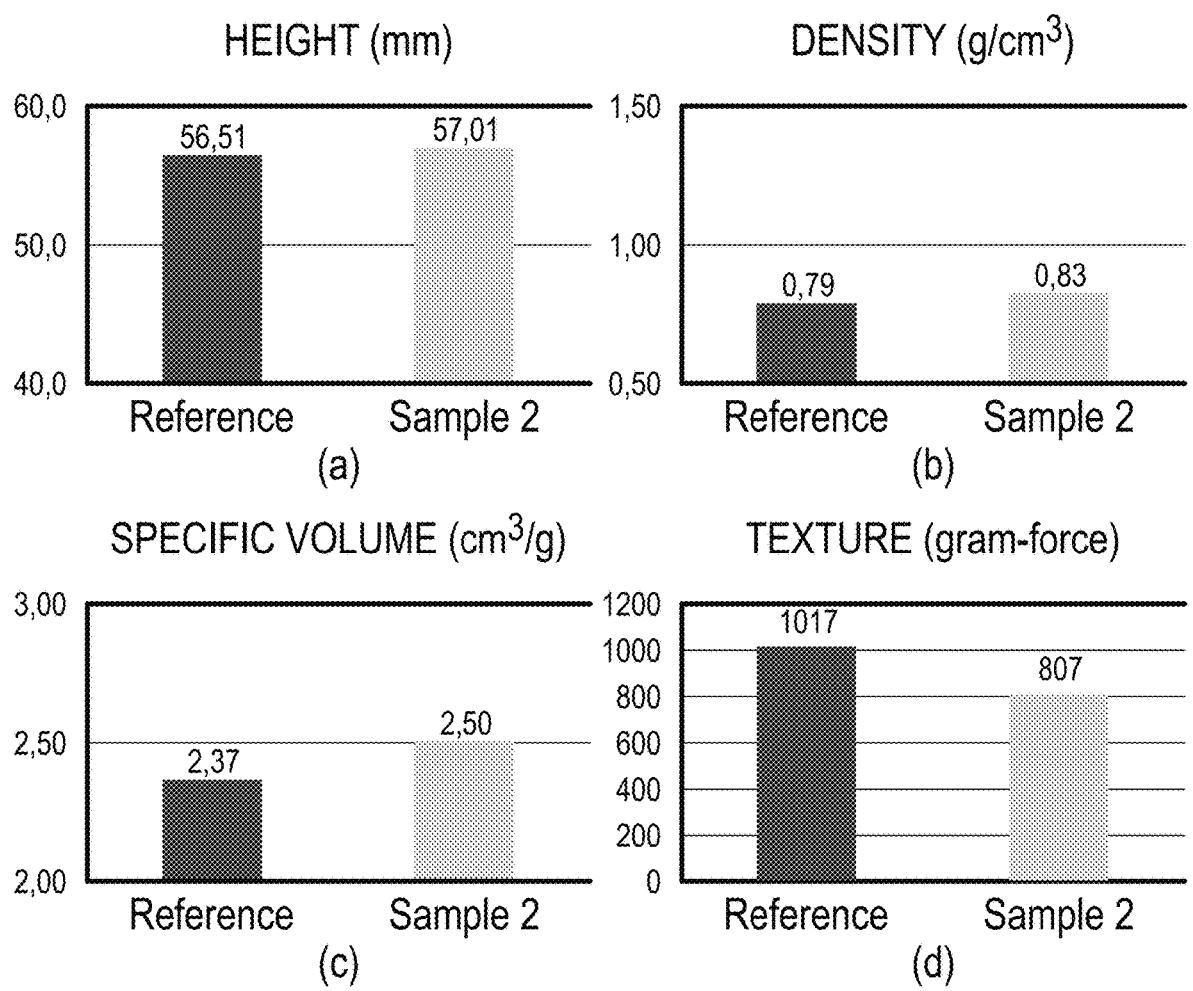
FIG. 9 indicate comparative data between cakes prepared through pre-mixture formulations. The reference sample uses hydrogenated fat, based on palm, with 57% of saturated fats, 3% trans fats and a mixture of fatty acid mono- and di-glyceride emulsifier and propylene glycol ester (of commercial use). The test sample, called Sample 2, uses a structured fat composition, based on soybean and palm, with 32% of saturated fats, 2% trans fats, a mixture of fatty acid mono- and di-glyceride emulsifier and propylene glycol ester and 5% emulsifier (52% of monoacylglycerol).

The samples evaluated obtained results very close to the reference sample, thus characterizing the maintenance of the physical characteristics of the product, while improving the nutritional quality. The results of the sensorial tests can be found in the graph ion FIG. 8.

Comparative Example for Pre-Mixed Cake Dough

For comparative purposes, one prepared formulations comprising a reference fat or a test sample for cake dough in the pre-mixing cake baking pan. The formulations followed the proportions below:

TABLE 3

Formulation of cake pre-mixture in base percentage of wheat flour

| Ingredients | Percentage, base wheat flour |
|---|---|
| Wheat flour | 100.0 |
| Sugar | 95.9 |
| Reference/test sample | 14.7 |
| Starch | 2.9 |
| Yeast | 5.9 |
| Salt | 0.4 |

As reference, one used a hydrogenated fat, base palm, with 57% of saturated fats, 3% of trans fats by weight based on the total weight of the hydrogenated fat, and a mixture of fatty acid mono- and di-glycerides emulsifier and propylene glycol ester (commercial use).

The test sample of the invention, called Sample 2, used comprises a structured fat composition, base soybean an palm, with 32% of saturated fats, 2% of trans fats, a mixture of mono- and di-glycerides of fatty acids and propylene glycol ester and 5% of emulsifier (52% of monoacylglycero by weight based on the weight of emulsifier) by weight based on the weight of the structured fat composition.

For the preparation of the cake using the pre-mixture, one followed the conventional steps for preparing a cake. Initially the reference fat or the test sample was incorporated into the sugar, then one mixed the powders: flour, salt, chemical yeast and starch, then added eggs and milk on the weight of the pre-mixture according to the recipe, the mixture was beaten under constant velocity for 7 minutes.

In order to guarantor homogeneity between the cakes prepared, the mixtures were weight in the baking pans.

The baking was carried out in baking oven at 180° C. for 43 minutes.

The cakes using the reference fat and the structured fat composition of the present invention were compared as to the height, density, specific volume and texture.

As can be seen in FIGS. (a)-9(d), the values obtained for the test sample were very close to the reference, thus proving the maintenance of the physical characteristics of the product, while improving the nutritional quality.

Comparative Example for English-Cake Dough

For comparative purposes, one prepared formulations comprising a reference fat or a test sample for English-cage dough. The formulations followed the proportions below:

TABLE 4

Formulation of English cake in percentage base wheat flour

| Ingredients | Percentage, base wheat flour |
|---|---|
| Wheat flour | 100.0 |
| Water | 62.0 |
| Egg | 60.0 |
| Sugar | 59.6 |
| Reference/test sample | 19.2 |
| Powdered milk | 9.6 |
| Sorbitol | 5.0 |
| Salt | 0.7 |
| Baking soda | 1.0 |
| Double aluminum and sodium phosphate | 1.0 |
| Calcium propionate | 0.3 |
| Aroma | 0.8 |

As reference, one used a hydrogenated fat, base palm, with 57% saturated fats, 3% trans fats by weight based on the total weight of the hydrogenated fat, and a mixture of fatty acid mono- and di-glyceride emulsifiers and propylene glycol ester (commercial use).

The test sample of the invention used comprises a structured fat composition, base soybean and palm, with 32% saturated fats, 2% trans fats, a mixture of fatty acid mono- and di-glyceride emulsifier and propylene glycol ester, and 5% emulsifier (52% monoacylglycerol by weight based on the total weight of the emulsifier) by weight based on the weight of the structured fat composition.

The process of preparing English cake was conducted as described hereinafter.

At first called "cream phase", the reference fat or test sample was mixed with sugar and the aroma under constant stirring for 21 minutes. Then one added eggs to the "aeration phase", which comprises stirring with greater intensity for 3 minutes.

Finally, one added flour, powdered milk, baking powder, double aluminum phosphate and calcium propionate, as well as water and sorbitol, during the beating phase, which consists in stirring with less intensity, more specifically the same "cream phase" for 7 minutes.

In order to guarantee homogeneity between the cakes prepared, the mixtures were weighed in the baking pans.

The baking process was carried out in a baking oven at 180° C. for 43 minutes.

The cakes using the reference fat and the structured fat composition of the present invention were compared for height, density, specific volume and texture.

Figure 10:
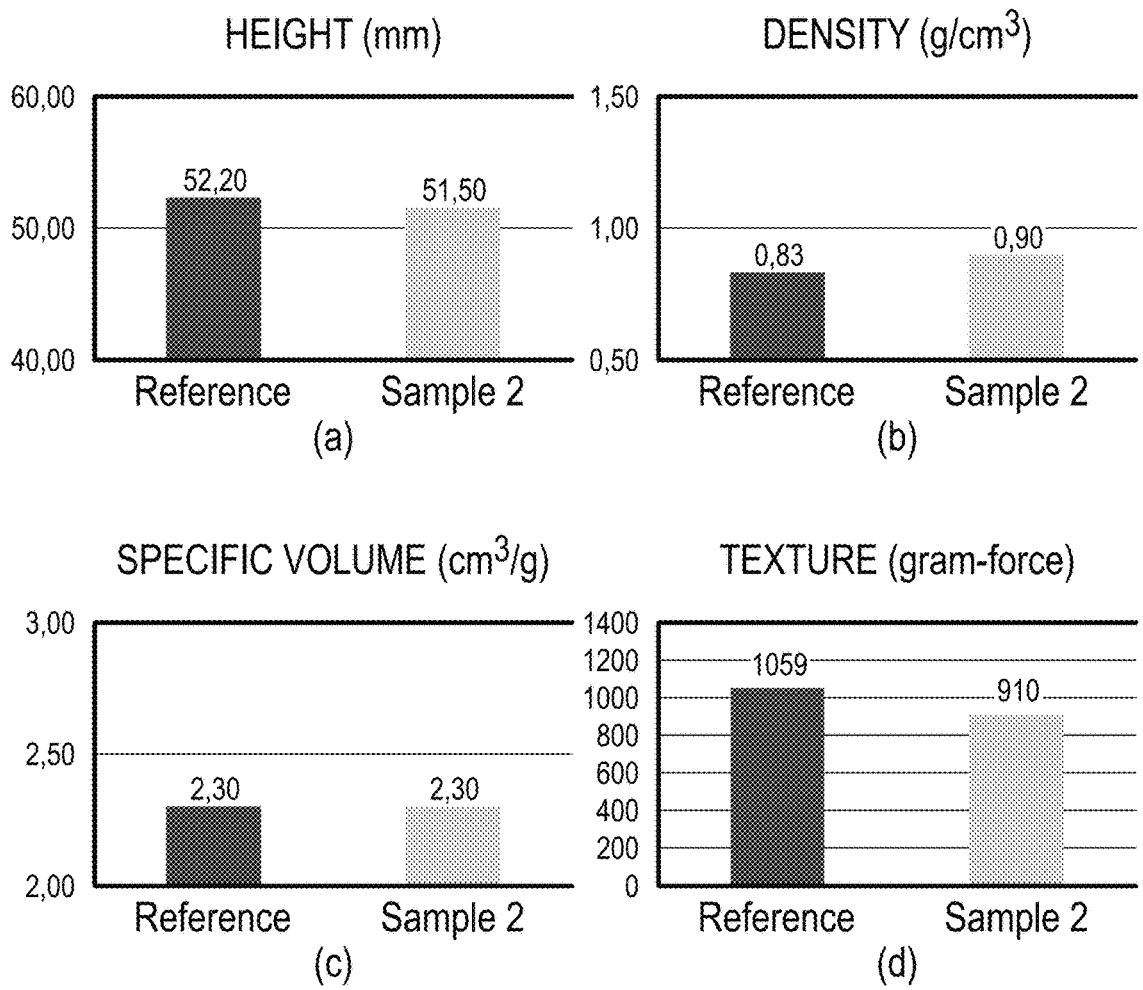
FIG. 10 indicate comparative data between formulations of English cake. The reference sample used hydrogenated fat, based on palm, with 57% of saturated fats, 3% trans fats and a mixture of fatty acid mono- and di-glyceride emulsifier and propylene glycol ester (commercial use). The test sample, called Sample 2, used a structured fat composition, based on soybean and palm, with 32% saturated fats, 2% trans fats, a mixture of fatty acid mono- and di-glyceride emulsifier and propylene glycol ester and 5% of emulsifier (52% of monoacylglycerol).

As can be seen from FIGS. 10(a)-10(b), the values obtained by the test sample were very close to the reference, thus proving the maintenance of the physical characteristics of the product, while improving the nutritional quality.

Comparative Example for English-Cake Dough

For comparative purposes, one prepared formulations for ice creams comprising a reference fat and a test sample, according to the formulation below:

TABLE 5

Ice-cream formulation using reference fat in percentage

| Ingredients | % |
|---|---|
| Water | 63.45 |
| Sugar | 13.75 |
| Skim powdered milk | 8.75 |
| Reference sample | 8.40 |

TABLE 5-continued

Ice-cream formulation using reference fat in percentage

| Ingredients | % |
| --- | --- |
| Dehydrated glucose | 3.75 |
| Partially demineralized whey | 1.25 |
| Stabilizing system | 0.65 |

TABLE 6

Ice-cream formulation using test sample in percentage

| Ingredient | % |
| --- | --- |
| Water | 62.85 |
| sugar | 13.75 |
| Skim milk | 9.75 |
| Test sample (sample 03) | 5.00 |
| Dehydrated glucose | 4.25 |
| Maltodextrin | 2.00 |
| Partially demineralized whey | 1.75 |
| Stabilizing system | 0.65 |

As reference, one used a commercial palm oil with 50% saturated and 2% trans fat by weight based on the total weight of the commercial palm oil.

As test sample, called sample 03, one sued a structured fat composition, soybean and palm, with 25% saturated fats, 2% trans fat and 7% emulsifier (52% monoacylglycerol by weight based on the total weight of the emulsifier) by weight based on the total weight of the structured fat composition.

The process of preparing the ice creams was the conventional process which comprises heating up to 70° C. water with the powdered ingredients to obtain the molten fat. Then one carries out a homogenization process by stirring under pressure, initially under 200 bar and then under 50 bar.

The molten fat product is then pasteurized at 85° C. for 15 seconds and then cooled down to 4° C., where maturation takes place. The maturation process of the syrup obtained lasts for 4 hours.

Once the syrup has maturated, the mixture is then subjected to a beating step, and then a hardening step, where it is kept at −50° C. for 24 hours.

After the product has hardened, it is stored at −18° C.

In order to compare the ice cream obtained by using the reference fat with the ice cream obtained by using the structured fat composition of the present invention, one carried out an Overrun test, wherein the percentage of incorporation of air into the ice cream is measured. This parameter is considered essential to the market characteristics, this being often the first parameter measured, since there are modifications in the formulation of an ice cream.

The results achieved are shown in the following table:

TABLE 7

Results of the Overrun test between ice cream containing reference fat and ice cream containing test sample of structured fat composition:

| Sample | Overrun (%) |
| --- | --- |
| Reference | 106.36 ± 0.89 |
| Sample 03 | 92.34 ± 3.95 |

As a result, it is possible to observe that the test sample of structured fat composition achieved a result very close to the sample containing reference fat, being very close to the 100% and, therefore, meeting the characteristics required by the market.

Figure 11:
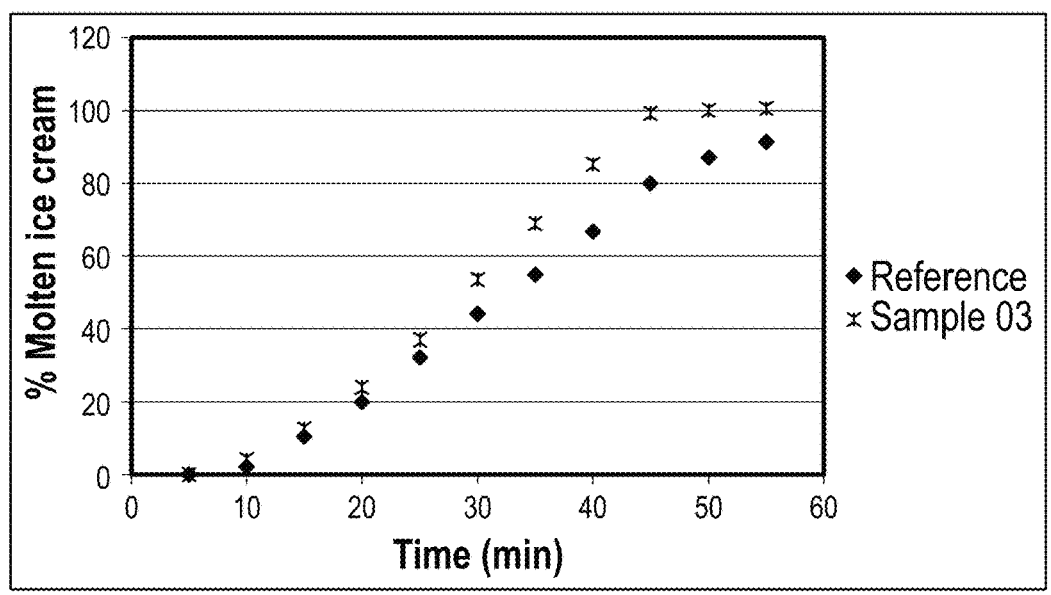
FIG. 11: a comparative graph of the melting of the ice-cream samples using reference sample containing commercial palm oil with 50% saturated and 2% trans fat and test sample, called Sample 03, comprising a structured fat composition, based on soybean and palm, with 25% saturated fats, 2% trans fat and 7% emulsifier (52% of monoacylglycerol). The results are expressed in percentage of melting per time in minutes.

A comparative curve of the ice-cream melting was further constituted, which is shown in FIG. 11. It is possible observe the behavior of the samples of ice cream was very similar, the sample that used test sample of the structured fat composition having achieved a melting profile a little slower when compared with the sample with the reference oil.

A preferred example of embodiment having been described, one should understand that the scope of the present invention embraces other possible variations, being limited only by the contents of the accompanying claims, which include the possible equivalents.

The invention claimed is:

1. A structured vegetable fat composition, characterized by comprising:
    i) 1-15% by weight of an emulsifier, based on the total weight of the composition, the emulsifier being derived from totally hydrogenated vegetable oils, wherein the emulsifier consists of a mixture consisting of monoacylglycerols and diacylglycerols and optionally propylene glycol ester, and wherein the emulsifier ranges from 52 to 99% of monoacylglycerols by weight, based on the total weight of the emulsifier; and
    ii) at least one refined vegetable oil selected from refined vegetable oils, which may or may not include fractioned and/or hydrogenated products,
    wherein:
        said structured composition contains maximum limit of 2% of trans fatty acids and exhibits contents of saturated fatty acid from 25% to 45% by weight, based on the total weight of the composition; and
        said structured composition exhibits crystallization in about 5 minutes at a temperature of 25° C. and reaches stabilization of the maximum contents of solids in up to 30 minutes when used in a food product.

2. The structured vegetable fat composition according to claim 1, characterized in that the amount of vegetable oils ranges from about 85 to 99% by weight based on the total weight of the composition.

3. The structured vegetable fat composition according to claim 1, characterized in that the vegetable oils comprise oleic and linoleic fatty acids.

4. The structured vegetable fat composition according to claim 1, characterized by comprising a mixture of fatty acids mono- and di-glyceride emulsifier and propylene glycol ester.

5. A product, characterized by comprising a structured fat composition as defined in claim 1.

6. A food product according to claim 5, characterized by exhibiting the behavior of:
    a. keeping the texture at a temperature ranging from 20 to 30° C.; and/or
    b. crystallizing, in about 5 minutes at a temperature of 25° C., reaching stabilization of the maximum contents of solids in up to 30 minutes; and/or
    c. exhibiting better consistency and being capable of remaining solid even at body temperature; and/or
    d. providing better incorporation of ingredients and air into the dough during the beating process; and/or
    e. imparting thermal stability to the product, wherein no separation of oil takes place along the whole shelf-life.

7. The food product according to claim 6, characterized in that:
    i. when the food product exhibits the behavior (a) and (b), it is selected from margarines, melanges, ice creams, and fillings of bonbons, biscuits;

ii. when the food product exhibits the behavior (b), it is broth in cubes;
iii. when the food product exhibits the behavior (c), it is selected from cakes, bonbons, and biscuits;
iv. when the food product exhibits the behavior (d), it is selected from cake dough; panettone dough; and cookie dough;
v. when the food product exhibits the behavior (e), it is selected from sweet creams, including hazelnut cream, chocolate-taste cream, cracking-type cream, peanut cream.

8. A structured vegetable fat composition, characterized by comprising:
   i) 1%-15% by weight of an emulsifier, based on the total weight of the composition, the emulsifier being derived from beta compatible totally hydrogenated vegetable oils, wherein the emulsifier consists of a mixture consisting of monoacylglycerols and diacylglycerols and optionally propylene glycol ester, and wherein the emulsifier contains 52% of monoacylglycerols by weight, based on the total weight of the emulsifier; and
   ii) at least one refined vegetable oil selected from refined vegetable oils, which may or may not include fractioned and/or hydrogenated products,
   wherein:
      said structured composition contains maximum limit of 2% of trans fatty acids and exhibits contents of saturated fatty acid from 25% to 45% by weight, based on the total weight of the composition; and
      said structured composition exhibits crystallization in about 5 minutes at a temperature of 25° C. and reaches stabilization of the maximum contents of solids in up to 30 minutes when used in a food product.

9. The structured vegetable fat composition according to claim 1, characterized by comprising from 2% to 10% by weight of the emulsifier, based on the total weight of the composition.

* * * * *